United States Patent [19]
Kienzle et al.

[11] Patent Number: 5,709,706
[45] Date of Patent: Jan. 20, 1998

[54] SURGICAL INSTRUMENT

[75] Inventors: Karl-Ernst Kienzle, Tuttlingen; Rupert Mayenberger, Rielasingen; Markus Nesper, Tuttlingen; Dieter Weisshaupt, Immendingen, all of Germany

[73] Assignee: Aesculap AG, Tuttlingen, Germany

[21] Appl. No.: 774,901

[22] Filed: Dec. 27, 1996

Related U.S. Application Data

[63] Continuation of PCT/EP95/01718, May 5, 1995.

[30] Foreign Application Priority Data

Jun. 28, 1994 [DE] Germany ............... 44 22 621.7

[51] Int. Cl.⁶ .......................... A61B 17/28; A61B 17/10
[52] U.S. Cl. ............................ 606/205; 606/142
[58] Field of Search ............. 606/1, 138–150, 606/167, 170, 174, 205–211, 51, 52

[56] References Cited

U.S. PATENT DOCUMENTS

| | | | |
|---|---|---|---|
| 3,750,652 | 8/1973 | Sherwin . | |
| 5,308,358 | 5/1994 | Bond et al. | 606/207 |
| 5,571,137 | 11/1996 | Marlow et al. | 606/205 |

FOREIGN PATENT DOCUMENTS

| | | |
|---|---|---|
| 0 546 767 | 6/1993 | European Pat. Off. . |
| 25 06 471 | 8/1975 | Germany . |
| 31 19 550 | 12/1982 | Germany . |
| 43 12 284 | 11/1993 | Germany . |
| 42 23 162 | 1/1994 | Germany . |
| WO 93/22980 | 11/1993 | WIPO . |
| WO 93/25267 | 12/1993 | WIPO . |

*Primary Examiner*—Glenn K. Dawson
*Attorney, Agent, or Firm*—Barry R. Lipsitz

[57] ABSTRACT

A surgical instrument including a shank, at least one tool mounted for swivel movement at the end of the shank, a swivel element mounted for swivel movement about an axis of rotation for swivelling the tool between an open position and a closed position, and an actuating member actuatable from an end of the shank located opposite the tool for swivelling the swivel element about the axis of rotation. The high closing forces required for plastic deformation of objects can also be achieved without excessive forces being transmitted to the drive mechanisms. The actuating member is an arm which is articulatedly connected at a first articulation point to the swivel element, and that in the open position of the tool, the arm be at an incline to an axis of the swivel element extending perpendicularly to the axis of rotation through the first articulation point and in the closed position of the tool, be essentially perpendicular to the axis of the swivel element.

17 Claims, 5 Drawing Sheets

SURGICAL INSTRUMENT

This application is a continuation of International PCT Application No. PCT/EP95/01718, filed on May 5, 1995.

BACKGROUND OF THE INVENTION

The present invention relates to a surgical instrument.

A surgical instrument with a shank having mounted for swivel movement at the end thereof tools which can be swivelled between an open position and a closed position by swivel elements mounted for swivel movement about an axis of rotation is known from German laid-open paper DE 43 12 284 A1. The swivel elements can be swivelled with the aid of an actuating member about the axis of rotation, the actuating member being actuatable from an end of the shank located opposite the tools and comprising two arms which are each articulatedly connected to a swivel element at a first articulation point. This known instrument is provided with tools made of plastic which have a high flexibility and yield distinctly when they encounter resistance.

In German laid-open paper DE 25 06 471 it is suggested that swivel element and arm be aligned in relation to each other such that in the open position of the tool, the arm is at an incline to an axis of the swivel element extending perpendicularly to the axis of rotation through the first articulation point, and in the closed position of the tool, is essentially perpendicular to the axis.

However, the design known from German laid open paper DE 25 06 471 has the disadvantage that to close the tool, on the one hand, the actuating element displaceable within the shank has to be displaced, and, on the other hand, a guide sleeve surrounding the shank also has to be displaced. Only in this way is it possible to achieve a large angular spacing between the positions of the swivel element in the open and closed positions. Thus, the handling of the known surgical instrument for opening and closing the tool is rather difficult.

The object of the present invention is, therefore, to so design a surgical instrument of the generic kind that with simple handling of the surgical instrument, a particularly large angular spacing between the positions of the swivel element in the open and closed positions is achievable.

SUMMARY OF THE INVENTION

This object is accomplished in accordance with the invention in a surgical instrument of the kind described at the outset by the length of the arm corresponding almost to the inner width of the shank.

This design makes it possible, by means of a force acting along the arm on the swivel element, to produce a torque acting on the swivel element which increases during the transition from the open to the closed position and is at its maximum in the closed position. Consequently, the torque acting on the tool and the closing force also increase during the transition from the open to the closed position. As a rule, the deformation forces required for the plastic deformation of an object also increase during the transition from the open to the closed position. This construction thus makes available the most favorable lever relations and hence the maximum torque acting on the swivel element, with a predetermined force transmitted along the arm, precisely at that point in time when it is required, namely when the tool is in the closed position.

When the tool is in the open position, the arm is at an incline to the shank axis and when the tool is in the closed position, the arm is almost perpendicular to the shank axis.

With a constant displacement speed of the transmission member, the angular speed of the swivel element and hence of the tool thus decreases as the closed position is approached, and, therefore, particularly fine adjustment of the position of the tool in the proximity of the closed position is possible.

As the arm is almost perpendicular to the shank axis when the tool is in the closed position and the length of the arm almost corresponds to the inner width of the shank, by displacement of the second articulation point parallel to the shank axis, the first articulation point can be moved transversely to the shank axis from a position near an inside wall of the shank to a position near an opposite inside wall of the shank. This results in a particularly large angular spacing between the positions of the swivel element in the open and closed positions.

In a preferred embodiment, provision is made for the arm to be articulatedly connected with its free end at a second articulation point to a transmission member which is displaceable along the shank axis. This results in a very simple conversion of a push-pull movement which can be transmitted directly along the shank to a rotary movement of the swivel element. The force acting through the arm on the swivel element acts along an arm axis extending through the first and the second articulation points of the arm.

In all embodiments of the inventive surgical instrument it is advantageous for the radial spacing of the first articulation point from the axis of rotation to be considerably larger than the inner width of the shank. This results in a long lever arm for the force acting along the arm on the swivel element.

The type of coupling between the swivel element and the tool has not yet been explained in detail.

The swivel element can be rigidly connected to the tool. In this case, tool and swivel element are swivelled about a common axis of rotation. This construction has the advantage of great simplicity and low frictional losses as additional gear means are dispensed with.

However, the swivel element can also be connected to the tool via gear means if, for example, the angular speed of the tool in relation to that of the swivel element is to be reduced/increased or the direction of rotation of the tool in relation to that of the swivel element is to be changed.

A surgical instrument according to the invention advantageously comprises two tools which can be swivelled in opposite directions, with the swivel element swivelling the one tool and the arm swivelling the swivel element being arranged symmetrically in relation to a swivel element swivelling the other tool and an arm swivelling this swivel element in terms of rotation through 180° about the shank axis. Both tools are driven in the same way, and, therefore, the statements made hereinabove and hereinbelow on the drive relate to both tools.

To enable gripping or plastic deformation of objects, it is expedient for the tool or tools to comprise forceps jaws which with a forceps jaw of a tool swivelling in the opposite direction or with a stationary forceps jaw form forceps which in the open position of the tool or tools are open further than in the closed position.

If a minimum expansion of the objects to be gripped or plastically deformed by the forceps is predetermined, it is expedient for the forceps jaws to be spaced from each other by the amount of this minimum expansion in the closed position in order that the closed position with its favorable lever relations can actually be attained when the surgical instrument is used in accordance with the given specifications.

Further features and advantages of the invention are the subject matter of the following description and the drawings of an embodiment.

DETAILED DESCRIPTION OF THE INVENTION

Figure 1:
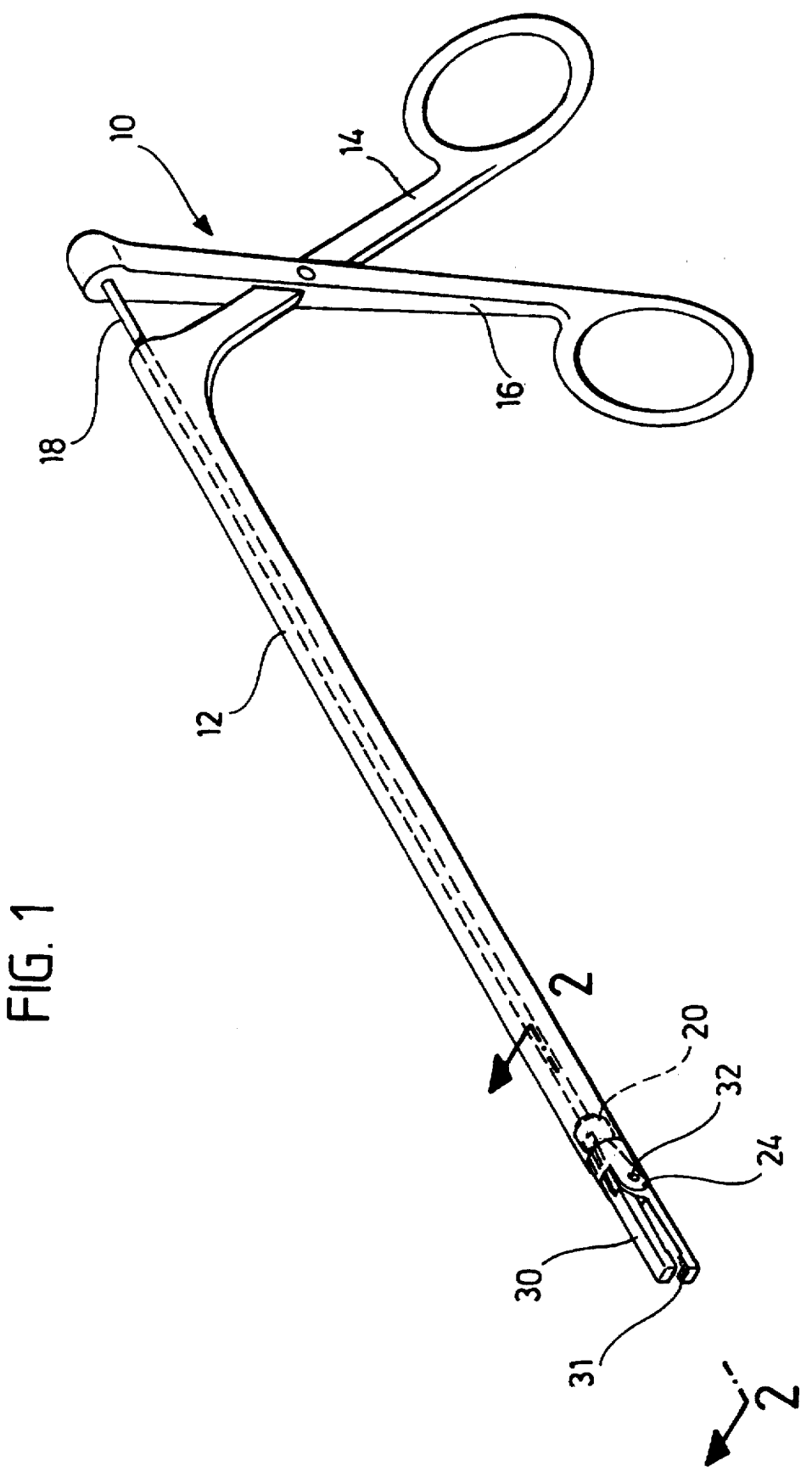
FIG. 1 a perspective view of a surgical instrument with tools in an open position.
Figure 2:
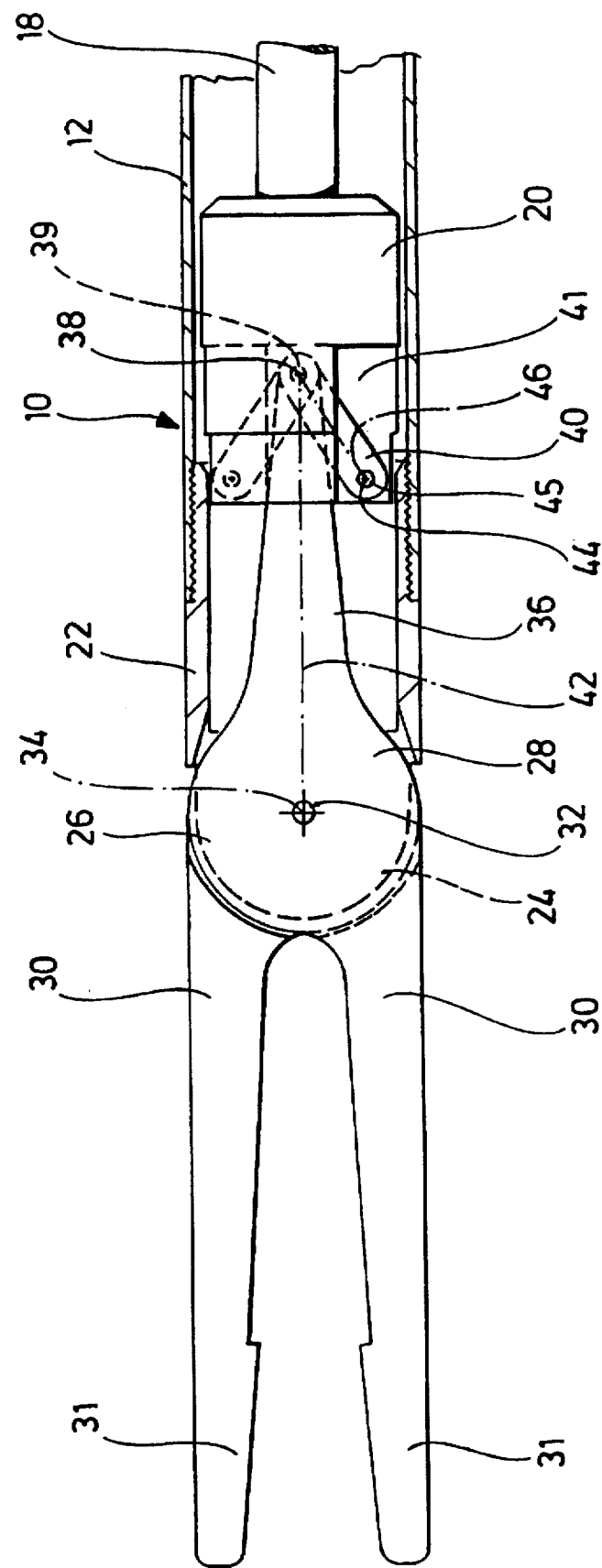
FIG. 2 a longitudinal section through part of the surgical instrument on the tool side thereof, taken along line 2—2 in FIG. 1.
Figure 3:
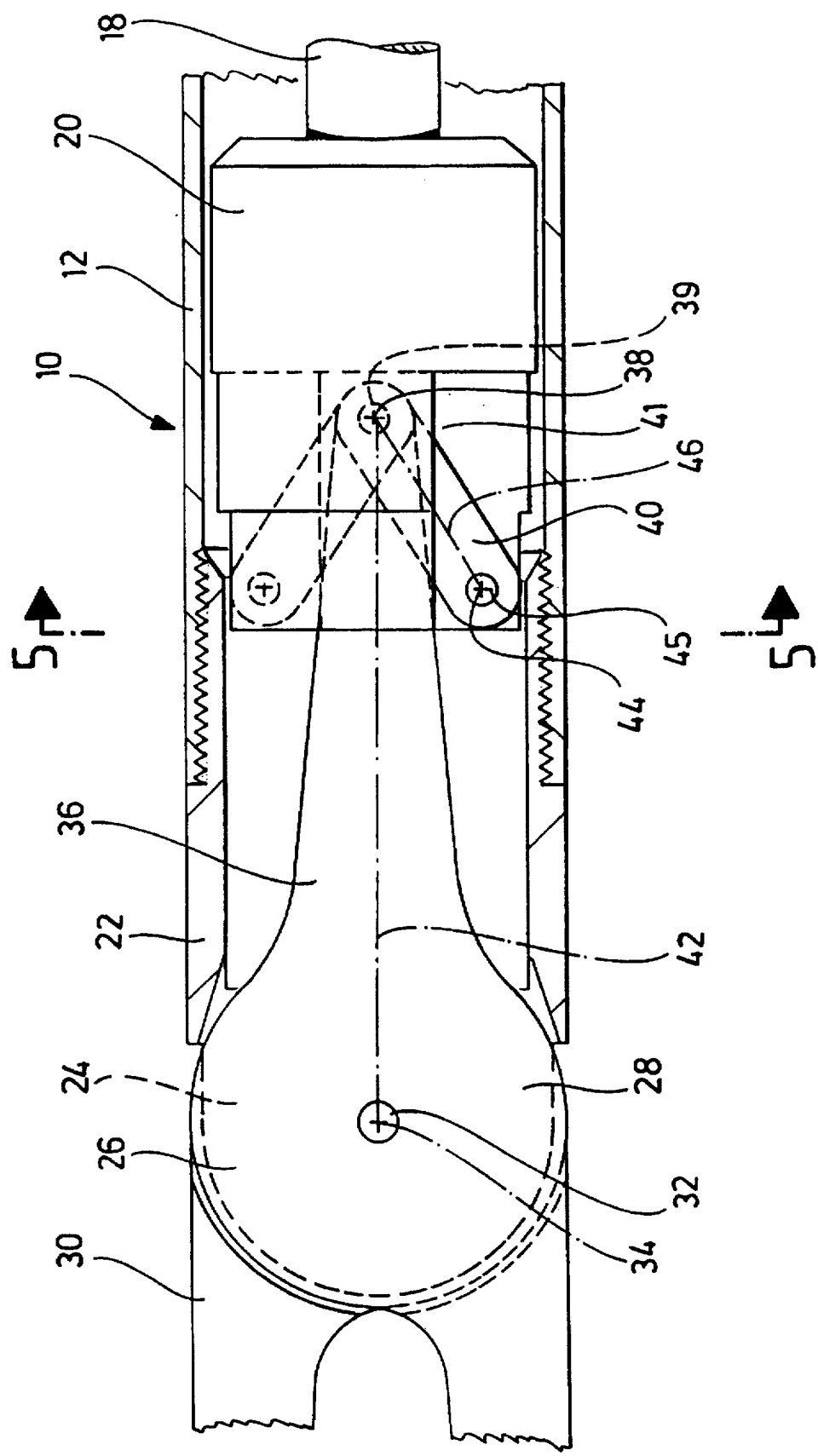
FIG. 3 an enlarged section from FIG. 2.

The surgical instrument shown in the drawings and designated in its entirety 10 comprises a tubular shank 12 which at its rear end continues into an integrally formed handle 14 protruding essentially transversely. Articulatedly connected to the handle 14 is a further handle 16 which, in turn, is articulatedly connected to a push-pull rod 18. The push-pull rod 18 extends through the shank 12 and is connected in the front part of the shank 12 to an essentially cylindrical transmission member 20 which is longitudinally displaceable in the shank 12.

Screwed into a front end of the shank 12 is a tubular connector 22 which forms an extension of the shank 12 and carries at its front end two bearing members 24 located opposite each other.

These bearing members 24 form between them a space 26 into which the rear ends 28 of two tools 30 of identical design protrude. These tools 30 can have, for example, at their front ends forceps jaws 31 which together form a pair of forceps. They are mounted in the bearing members 24 by means of a pin 32 penetrating these for swivel movement about an axis of rotation 34 which is oriented perpendicular to the axis of the tubular connector 22.

Each of the tools 30 carries at its rear end 28 a swivel lever 36 which extends through the tubular connector 22 and protrudes into the shank 12.

Each swivel lever 36 is articulatedly connected to an arm 40 by a first articulation pin 39 at a first articulation point 38.

The verticals to the axis of rotation 34 through the first articulation points 38 are referred to hereinbelow as swivel lever axes 42.

Each arm 40 protrudes into a recess 41 at a front end face of the transmission member 20 and at its free end is articulatedly connected to the transmission member 20 by a second articulation pin 45 at a second articulation point 44.

The straight lines fixed by the first articulation point 38 and the second articulation point 44 of each arm 40 are referred to hereinbelow as arm axes 46.

The moveable parts of the surgical instrument 10 each have an open position which corresponds to an open position of the tools 30 and a closed position which corresponds to a closed position of the tools 30.

The open position is illustrated in FIGS. 1 to 3, 5 and 6.

In the open position, the tools 30 are turned to the maximum extent in opposite directions about the axis of rotation 34. The forceps formed by the tools 30 with the forceps jaws 31 are open to the maximum extent in the open position.

In the open position, the swivel levers 36 are aligned essentially along the shank axis, i.e., the swivel lever axes 42 extend at a short distance from the shank axis parallel thereto.

In the open position, each arm 40 projects forwards at an incline from the associated swivel lever 36, i.e., the arm axes 46 form a small acute angle with the swivel lever axes 42, and the second articulation points 44 are arranged closer to the front end of the shank 12 than the first articulation points 38, near the inside wall of the tubular connector.

Owing to the acute angles between the arm axes 46 and the swivel lever axes 42, forces transmitted by the arms 40 along the arm axes 46 onto the swivel levers 36 only produce comparatively small torques acting on the swivel levers 36 and on the tools 30 rigidly connected thereto.

Figure 4:
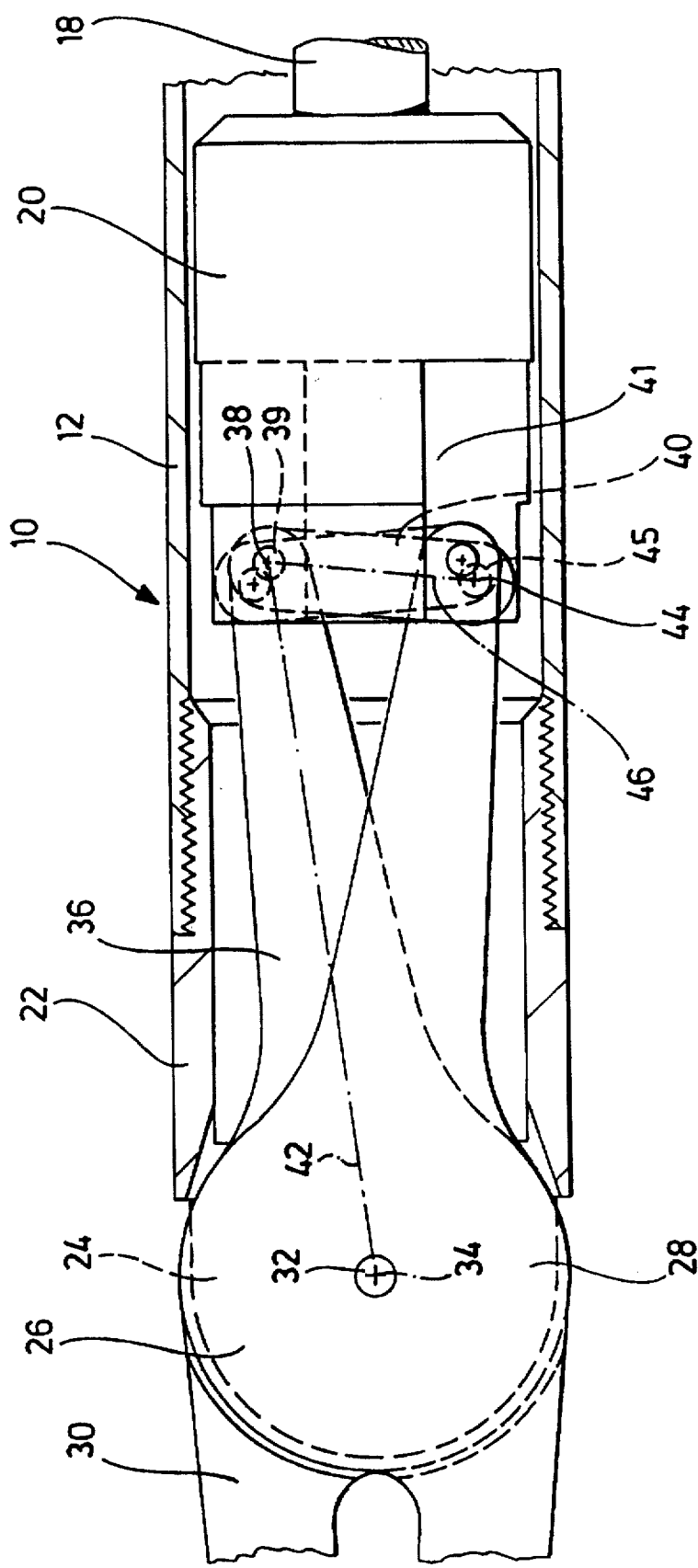
FIG. 4 a view similar to FIG. 3 with tools in a closed position.
Figure 5:
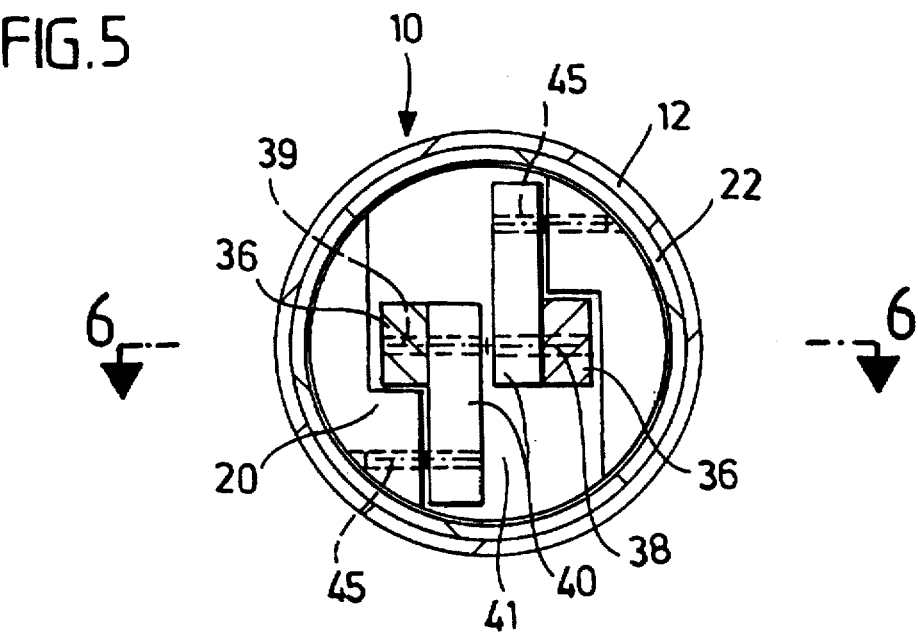
FIG. 5 a cross section through the shank of the surgical instrument, taken along line 5—5 in FIG. 3.
Figure 6:
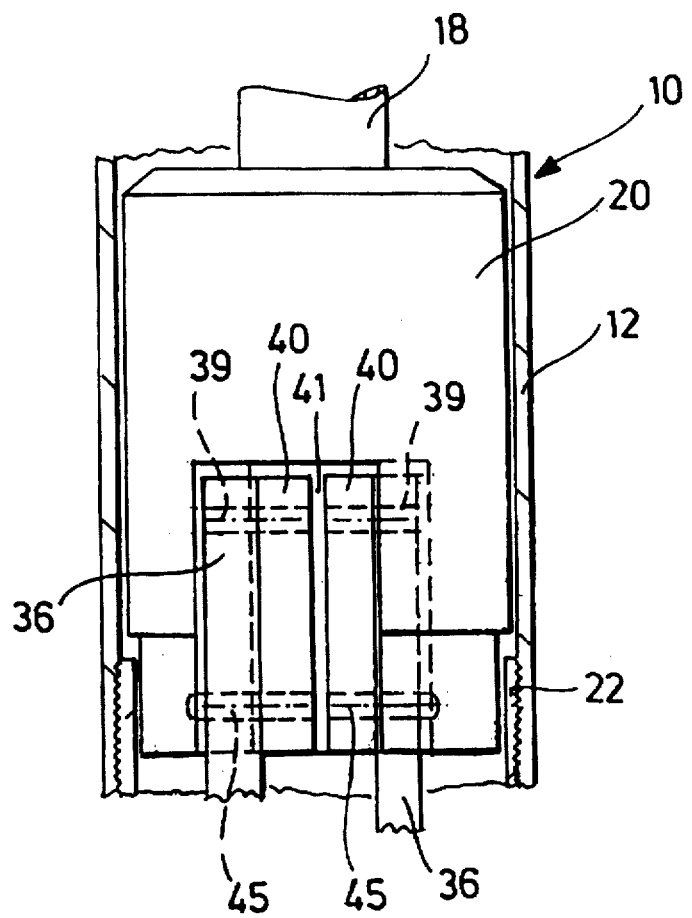
FIG. 6 a longitudinal section through a section of the shank of the surgical instrument, taken along line 6—6 in FIG. 5.

By spreading apart the handles 14 and 16, the moveable parts of the surgical instrument 10 are moved from the open position described hereinabove to the closed position illustrated in FIG. 4.

During this, the transmission member 20 is pulled rearwardly along the shank axis by the push-pull rod 18, whereby the second articulation points 44 are also displaced rearwardly parallel to the shank axis.

During the transition from the open to the closed position (during the closing), the arms 40 are swivelled about the second articulation points 44 until they are aligned almost perpendicular to the shank axis, i.e., until the arm axes 46 are almost perpendicular to the shank axis.

The swivel levers 36 and the tools 30 rigidly connected thereto are, in turn, thereby swivelled about the axis of rotation 34 and so the forceps jaws 31 of the tools 30 move towards each other and the forceps formed by the forceps jaws 31 close until the forceps jaws 31 rest against each other.

Since the radial spacing of the first articulation points 38 from the axis of rotation 34 is large in comparison with the length of the arms 40, the first articulation points 38 move essentially perpendicularly to the shank axis away from the shank center towards the wall of the shank 12 during the transition from the open to the closed position.

Owing to the closed position being reached before the arms 40 are aligned exactly perpendicular to the shank axis, reversal of the direction of movement of the first articulation points 38 during the closing and re-opening of the forceps formed by the forceps jaws 31 are prevented.

It is crucial that during the transition from the open to the closed position, the angles between the arm axes 46 and the swivel lever axes 42 extending through the same articulation point 38 increasingly approach right angles until they reach essentially 90°. The lever relations for the generation of torques acting on the swivel levers 36 and hence on the tools 30 thereby become more and more favorable during the closing, i.e., forces transmitted by the arms 40 along the arm axis 46 onto the swivel levers 36 generate increasing torques during the closing which are at their maximum in the closed position itself.

Such an increase in the torque during the closing is particularly favorable for plastic deformation of an object, for example, an operating clip made of plastic or metal, arranged between the forceps jaws 31, during the closing, because the counter-torques increasing during the deformation can be more easily compensated in this way.

If there is a predetermined minimum expansion of the objects to be gripped or the objects to be deformed after their deformation perpendicular to the shank axis, it is advantageous to design the tools 30 such that in the closed position, the forceps jaws 31 are spaced by the amount of this minimum expansion from each other. This ensures that the closed position with its favorable lever relations can actually be used during use of the surgical instrument 10.

In an alternative embodiment of a surgical instrument 10, not illustrated, in the open position, the arms 40 do not project forwards at an incline in the direction of the shank, but rearwards at an incline, from the respective swivel levers 36. In this case, for the transition from the open to the closed position, the handles 14 and 16 are moved towards each other so the transmission member 20 connected to the push-pull rod 18 is moved forwards in the direction of the shank and the arms 40 are swivelled about the respective second articulation points 44 until they are aligned almost perpendicular to the shank axis. In other respects, this alternative embodiment corresponds as regards design and function to those described hereinabove.

We claim:

1. A surgical instrument, comprising:

a shank having a longitudinal axis and an inner width;

at least one swiveling tool including a first tool which is mounted for swivel movement at the end of said shank;

a second tool which opposes said first tool;

a first swivel element which is mounted for swivel movement about an axis of rotation for swiveling said first tool in a range of motion between a first position and a second position; and a first actuating member actuatable from an end of said shank which is located opposite said first tool for swiveling said swivel element about said axis of rotation; wherein:

said first actuating member comprises an arm which is articulatedly connected to said first swivel element at a first articulation point;

said arm is adapted to position said first tool in said first position when said arm is at an incline to an axis of said first swivel element and at an incline to said shank axis;

said axis of said first swivel element extends perpendicularly to said axis of rotation through said first articulation point;

said arm is adapted to position said first tool in said second position when said arm is approximately perpendicular to said axis of said first swivel element and almost perpendicular to said shank axis; and a length of said arm corresponds almost to said inner width of said shank.

2. A surgical instrument as defined in claim 1, wherein:

said first position is away from said second tool and said second position is toward said second tool.

3. A surgical instrument as defined in claim 1, wherein:

said arm is articulatedly connected to a transmission member which is displaceable along said shank axis.

4. A surgical instrument as defined in claim 3, wherein:

said arm extends from a first end to a second end;

said first articulation point is proximate to said first end; and said arm is articulatedly connected at said second end to said transmission member.

5. A surgical instrument as defined in claim 1, wherein:

a radial spacing of said first articulation point from said axis of rotation is considerably larger than the inner width of said shank.

6. A surgical instrument as defined in claim 1, wherein:

said first swivel element is rigidly connected to said first tool.

7. A surgical instrument as defined in claim 1, wherein:

said first and second tools comprise respective forceps jaw portions.

8. A surgical instrument as defined in claim 1, wherein:

said second tool is stationary with respect to said shank.

9. A surgical instrument as defined in claim 1, wherein:

said second tool is mounted for swivel movement at the end of said shank and is adapted for swiveling in an opposite direction than said first tool.

10. A surgical instrument as defined in claim 9, further comprising:

a second swivel element which is mounted for swivel movement for swiveling said second tool; and a second actuating member which is actuatable from said end of said shank for swiveling said second swivel element.

11. A surgical instrument as defined in claim 10, wherein:

said second swivel element is mounted for swivel movement about said axis of rotation.

12. A surgical instrument as defined in claim 10, wherein:

said first and second swivel elements are arranged symmetrically in relation to said shank axis during at least a portion of a range of the swivel movement of said first and second swivel elements.

13. A surgical instrument as defined in claim 10, wherein:

said first and second tools comprise respective forceps jaw portions.

14. A surgical instrument as defined in claim 13, wherein:

said forceps jaw portions are spaced apart from one another even when said forceps jaw portions swivel toward each other to respective limits of their ranges of motion.

15. A surgical instrument as defined in claim 10, wherein:

said first position is away from said second tool and said second position is toward said second tool;

said second actuating member comprises an arm which is articulatedly connected to said second swivel element at a second articulation point;

said arm of said second actuating member is adapted to position said second tool toward said first tool when said arm of said second actuating member is at an incline to an axis of said second swivel element and at an incline to said shank axis; and said axis of said second swivel element extends perpendicularly to said axis of rotation through said second articulation point.

16. A surgical instrument as defined in claim 15, wherein:

said arm which swivels said first swivel element and said arm which swivels said second swivel element are arranged symmetrically in relation to said shank axis during at least a portion of a range of the swivel movement of said first and second swivel elements.

17. A surgical instrument as defined in claim 15, wherein:

said arm of said second actuating member is adapted to position said second tool away from said first tool when said arm of said second actuating member is approximately perpendicular to said axis of said second swivel element and almost perpendicular to said shank axis.

* * * * *